United States Patent [19]

Haddad

[11] 4,320,761

[45] Mar. 23, 1982

[54] SURGICAL DEVICE FOR EXCISION OF TISSUE

[76] Inventor: Heskel M. Haddad, 1200 Fifth Ave., New York, N.Y. 10029

[21] Appl. No.: 177,706

[22] Filed: Aug. 13, 1980

Related U.S. Application Data

[63] Continuation of Ser. No. 9,894, Feb. 6, 1979, abandoned, which is a continuation of Ser. No. 763,490, Jan. 28, 1977, abandoned.

[51] Int. Cl.$^3$ ............................................. A61B 17/32
[52] U.S. Cl. .................................... 128/305; 128/276; 408/58
[58] Field of Search ...................... 128/305, 305.1, 276, 128/751–755, 24 A, 311; 408/56–59

[56] References Cited

U.S. PATENT DOCUMENTS

| | | | |
|---|---|---|---|
| 3,384,085 | 5/1968 | Hall | 128/305 |
| 3,526,219 | 9/1970 | Balamuth | 128/2 |
| 3,618,611 | 11/1971 | Urban | 128/305 |
| 3,732,858 | 5/1973 | Banko | 128/305 X |
| 3,734,099 | 5/1973 | Bender | 128/305 |
| 3,736,938 | 6/1973 | Evvard et al. | 128/305 |
| 3,776,238 | 12/1973 | Peyman et al. | 128/305 |
| 3,809,093 | 5/1974 | Abraham | 128/305 |
| 3,857,387 | 12/1974 | Shock | 128/24 A |
| 3,884,238 | 5/1975 | O'Malley | 128/305 |
| 3,906,954 | 9/1975 | Baehr et al. | 128/305 |
| 3,945,375 | 3/1976 | Banko | 128/305 X |
| 3,964,484 | 6/1976 | Reynolds et al. | 128/240 X |
| 3,976,077 | 8/1976 | Kerfoot | 128/305 |
| 3,996,935 | 12/1976 | Banko | 128/305 X |
| 4,014,342 | 3/1977 | Staub et al. | 128/305.1 |

OTHER PUBLICATIONS

Kaufman, "Vitrectomy from the Anterior Approach", *Ophthalmic Surgery*, vol. 6, No. 2, p. 58 (Summer, 1975).

*Primary Examiner*—Michael H. Thaler
*Attorney, Agent, or Firm*—Blum, Kaplan, Friedman, Silberman & Beran

[57] ABSTRACT

A surgical device for excision of tissue, the device being particularly suitable for removal of cataracts from the eye, includes a rotating stylus, a source of fluid for washing away excised tissue and a vacuum tube for removal of slurry consisting of excised tissue suspended in washing fluid. The assembly is small enough to be hand-held and insertable through a small incision.

11 Claims, 12 Drawing Figures

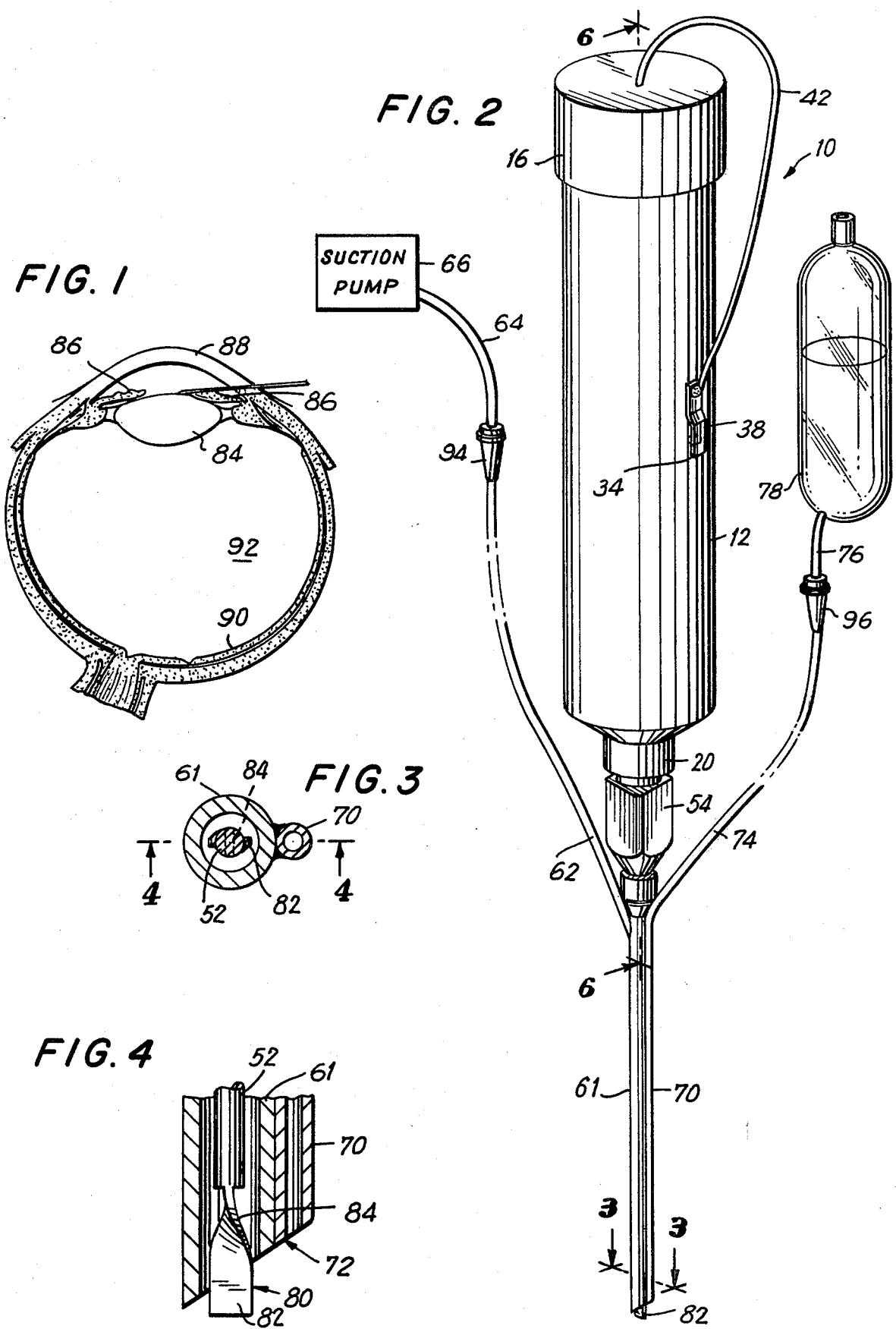

SURGICAL DEVICE FOR EXCISION OF TISSUE

This is a continuation, of application Ser. No. 9,894, filed Feb. 6, 1979, now abandoned which was a continuation of application Ser. No. 763,490, filed Jan. 28, 1977, now abandoned.

BACKGROUND OF THE INVENTION

In surgical practice occasions arise in which the scalpel is not the instrument of choice for removal of tissue. A particular case is the cataract operation so frequently necessary in the aged. A number of devices have been elaborated, such devices requiring special techniques. The principal difficulty encountered arises from the sides of such devices, it being necessary to introduce the operational portions of the device into the severely restricted portion of the eye which is to be worked on. Moreover, since the device used for removal of the cataract must be manipulated with great precision, any excess weight in the position of the device to be held in the hand of the surgeon can result in damage to the periphery of the working field. Consequently, a device which is effective for removal of tissue and yet which is light enough and small enough to be controllable by the surgeon with great precision is highly to be desired.

SUMMARY OF THE INVENTION

Three operational elements are combined in a single assembly to be inserted through an incision into a field from which tissue is to be removed. The assembly includes a cutter, i.e., a stylus on the end of a shaft, the stylus and shaft being rotatable with clearance within a hollow needle. A second hollow needle is joined to the hollow needle containing the shaft and stylus the ends of said two needles being coterminous and preferably bevelled in the same plane. The second needle is used for introduction of a washing fluid for flushing away tissue excised by the stylus. A tube is joined in a Y-connection to a region proximate the proximal end of said hollow needle containing the rotatable shaft. The purpose of the tube which is connected to a vacuum source or suction pump is to decrease the pressure in the annular space between the shaft and the hollow needle in which it rotates. As a result of the drop in pressure in said annular space, the slurry formed by the washing fluid and the excised tissue are drawn into said annular space and out through said Y-connection.

The shaft may be rotated by means of a flexible cable drive, but, preferably, by means of a motor mounted in a housing which is small enough so that it can be hand-held. The motor may be battery-powered, the battery being contained in the same housing as the motor or may be powered from a main. Another possibility is an air-driven motor, such a device being preferable where there is a danger of explosion. Means are provided for turning the motor on and off, for controlling the flow of washing fluid and for controlling the application of suction through the Y-connection.

Accordingly, an object of the present invention is a surgical device for the excision of tissue where the tissue removed is washed away as a slurry.

Another object of the present invention is a surgical device for the excision of tissue utilizing a rotating stylus for cutting, and a combination of a flow of washing fluid and suction for removal of excised tissue as a slurry in said washing fluid.

A further object of the present invention is a surgical device for the excision of tissue which is both small enough and light enough to be hand-held so that it can be manipulated with great precision.

Still another object of the present invention is a surgical device for the excision of tissue which can be used in extremely restricted regions with great precision and which requires only a small incision for insertion therethrough.

Yet another object of the present invention is a surgical device for the excision of tissue which is particularly suitable for cataract operations.

A significant object of the present invention is a method of excising tissue and removing said tissue during the excision of same by the use of flowing fluid and suction to remove the slurry formed by said flowing fluid and excised tissue.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a cross-sectional view of a human eye illustrating the insertion of the needle portion of the device in accordance with the invention;

FIG. 2 is a front perspective view of one embodiment of the device in accordance with the invention;

FIG. 3 is an enlarged sectional view taken along lines 3—3 of FIG. 2;

FIG. 4 is a fragmentary sectional view taken along lines 4—4 of FIG. 3;

DESCRIPTION OF THE PREFERRED EMBODIMENTS

Figure 5:
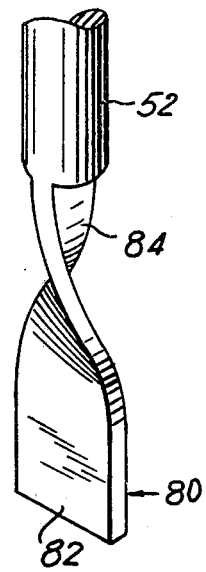
FIG. 5 is an enlarged perspective view of the stylus of the device of FIG. 2.

Referring now to FIGS. 2-6, a first embodiment of a surgical device for excision of tissue is depicted. The device 10 consists of a tubular housing 12 preferably formed of a plastic material of light weight. Housing 12 is open at one end and formed with a threaded outer wall region 14 at that open end. A correspondingly threaded cap 16 cooperates with threads 14 to close the open end of housing 12. The other end of housing 12 is partially closed by an end wall 18 substantially in the shape of a truncated cone terminating in a central opening 20 of circular cross-section. End wall 18 is also provided with an axially projecting portion 21 defining an annular socket 22 for the purpose more particularly described below. Received within housing 12 is a D.C. motor 24 powered by a D.C. battery 26 also received within housing 12. Motor 24 has two electrical terminals, an axial terminal 28 that is engaged by the positive terminal 30 of battery 26, and a terminal 32 joined by lead 33 to a contact 34 journaled through the wall of housing 12 and mounted on the exterior of the housing. The negative terminal of battery 26 is connected to a displaceable switch member 38 through spring 40 supported by cap 16 and lead 42 journaled through cap 16 into electrical connection with spring 40 at one end and electrically coupled to switch member 38 at rivet 44 at the other end. Rivet 44 serves to support switch member 38 as well as to provide the electrical connection between lead 42 and switch member 38. In this manner, motor 24 may be selectively actuated by depressing switch member 38 into engagement with contact 34. Motor 24 drives a drive shaft 46 which terminates in a socket member 48 having axially extending bore 50 therein. Press fit in socket 48 of drive shaft 46 is a shaft 52 which may be selectively removed from socket 48 if desired. The end of shaft 52 and the associated socket 48 may be provided with a non-circular cross-section (not shown) to ensure affirmative driving of shaft 52 if desired. Received within annular socket 22 of housing 12 is a fitting 54. Fitting 54 is formed with an axial passage 56 therethrough, through which shaft 52 extends. Fitting 54 is also provided with an annular sleeve portion 58 which is releasably received within slot 22 of housing 12. It should be noted that the fit between socket 48 of drive shaft 46 and projecting portion 21 of housing 12 is sufficiently tight to ensure an essentially waterproof seal to prevent the passage of water into the interior of housing 12.

Fixedly mounted on the outer end of fitting 54 is the enlarged end 60 of a first hollow needle 61, through which shaft 52 extends. A first tube 62 is joined to first needle 61 proximate the proximal end of needle 61, as by welding, there being an opening in the wall of needle 61 providing communication to first tube 62. As more particularly depicted in FIG. 2, first tube 62 communicates via line 64 to a suction pump 66. Separate controls may be provided for the selective actuation of suction pump 66, or if desired, the effective control thereof may be provided by one or more apertures 68 formed in first tube 62. The user of the device may selectively apply the suction force of suction pump 66 to the distal end of first needle 61 or permit such suction force to be dissipated at apertures 68 through manual selective obstructing or opening of apertures 68.

A second needle 70 is secured in side-by-side relation to first needle 61, as by welding. The distal end of said second needle is essentially flush with the distal end of said first needle and cut off in an inclined bevel 72, as more particularly shown in FIG. 4. A second tube 74 is joined to the end of second needle 70 and is connected through line 76 to a source of irrigation fluid such as bottle 78.

Shaft 52 terminates in a stylus 80 consisting of a thin flattened end region 82 joined to shaft 52 by a twisted region 84 (see FIGS. 4 and 5). The flattened end of stylus 80 projects slightly from the distal end of first and second needles 61, 70.

While the surgical device of FIGS. 2–6 can be utilized to excise any tissue, it is particularly adapted for use in connection with the surgical procedure for removal of a cataract from the human eye. A cataract is an opaque or partially opaque lens of an eye. The surgical procedure for the removal of a cataract by use of the instrument of FIGS. 2–6 will be explained in conjunction with the cross section of the human eye of FIG. 1. In FIG. 1, the lens 84 to be removed is supported behind the iris 86 and the cornea 88. The region between the lens and the retina 90 is filled with a jellylike substance referred to as the vitreous 92. In place of the large incision in the cornea normally required for cataract-removal surgery, a relatively small incision, dimensioned to receive first needle 61 and second needle 70, is formed in the cornea 88, and the distal ends of said needles are inserted through the incision to the region of the lens to be removed. The instrument is then turned on and shaft 52 is rotated by motor 24 to rotate stylus 80. Stylus 80 rotates and also experiences a slight oscillatory motion due to the clearance with the inner walls of first needle 61. The flattened end 82 of the stylus 80 serves to cut the lens material. During this operation, controlled amounts of irrigating fluid are passed into the region to be cut through second tube 74 and second needle 70, and suction is applied through first tube 62 and first needle 61 to draw out the cut lens material and the excess irrigation fluid, such material being initially carried out of the cutting region by the twisted region 84 of stylus 80. In this way, the fluid balance within the eye is also maintained. When all of the lens material has been removed, the instrument may be removed. The foregoing approach for cataract surgery using the surgical device in accordance with the invention offers material advantages over the prior art approaches in view of the small incision required in the cornea and the speed and efficiency with which the lens is broken up and drawn out of the eye by the light hand-held instrument. The flow of irrigating fluid may be controlled through manipulation of second tube 74 or through a valve (not shown).

In one embodiment, first needle 61 is formed of a No. 16 needle having an outer diameter of 0.07 inch and an inner diameter of 0.052 inch. Second needle 70 is formed of a 25 gauge needle having an outer diameter of 0.3 inch and an inner diameter of 0.18 inch. Shaft 52 is formed from a No. 19 stylet having an outer diameter of 0.038 inch. The flattened end 82 of the stylus 80 has a width of 0.047 inch, thereby providing a clearance with the inner diameter of first needle 61. The motor is a 2 volt, 250 mA D.C. motor. It should be noted that fitting 54, together with first and second needles 61, 70, and shaft 52 may be removed from the hand-held instrument for the purposes of sterilization, and a plurality of such fittings and shaft may be provided, thereby permitting the use of the instrument in a series of operations. It is also noted that first and second tubes 62 and 74 are respectively releasably coupled to lines 64 and 76 through releasable couplings 94 and 96 respectively.

Figure 7:
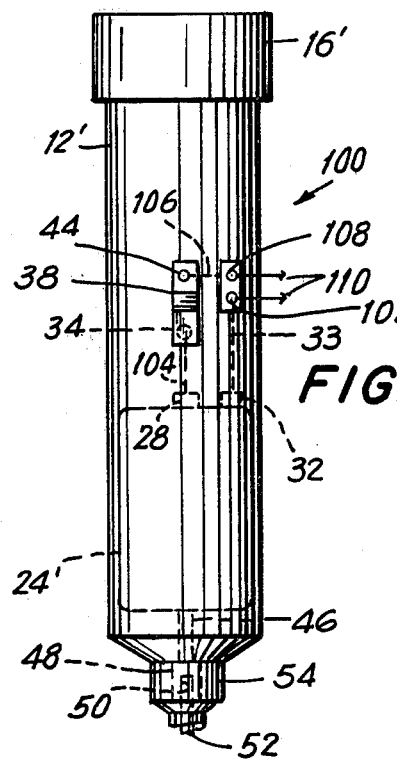
FIG. 7 is a fragmentary front elevational view of an alternate embodiment of the device of FIG. 2.
Figure 6:
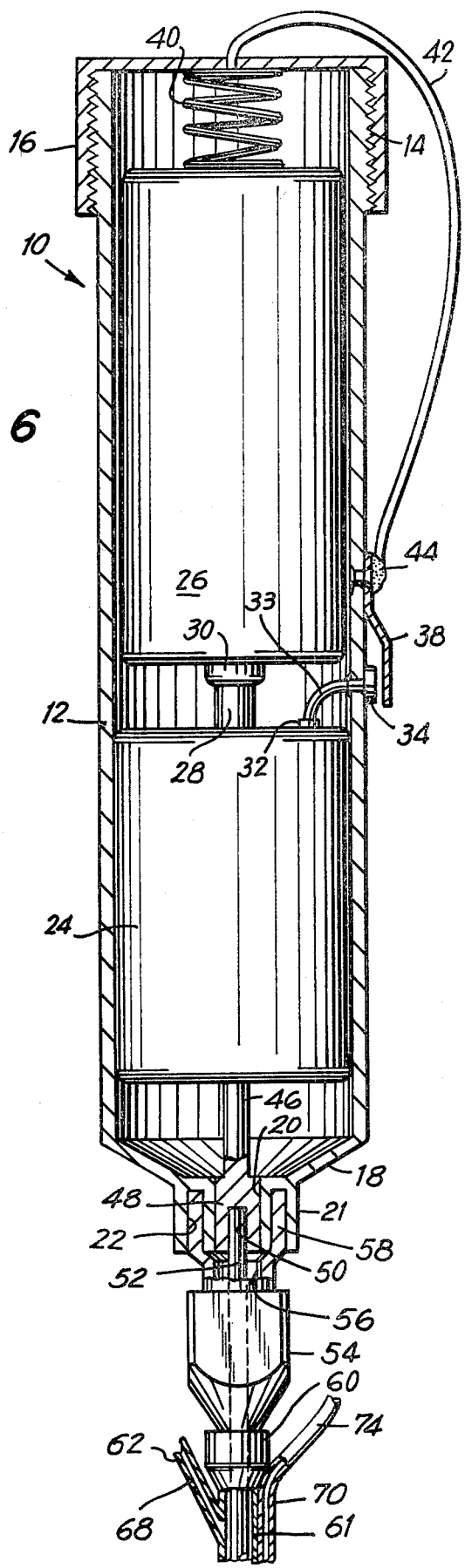
FIG. 6 is a cross-sectional view taken along lines 6—6 of FIG. 2.

Referring now to FIG. 7, an embodiment of the instrument of FIGS. 2–6 is depicted, like reference numerals being applied to like elements. In the embodiment of FIG. 7, an external power source is provided in place of the battery. Specifically, housing 12' and cover 16' enclose a motor 24' which may be of the A.C. or D.C. type. Central contact 28 of motor 24' is connected along line 104 to an exterior contact 34 which cooperates with switch member 38 to actuate the motor in the same manner as like elements in the embodiment of FIGS. 1-6. However, contact 32 is coupled by lead 33 to a first pin-socket terminal 102, while rivet 44 couples line 106 and switch member 38, line 106 being connected to a second pin-socket terminal 108. Pin-socket terminals 102 and 108 receive a conventional pin-type plug, as shown schematically by lines 110, for connection to an exterior power source which may be of any conventional type. By provision of voltage-control arrangements in the power source connected to lines 110, a speed-control arrangement may be provided. In all other respects, the instrument of FIG. 7 is identical to the instrument of FIGS. 1-6.

Referring now to FIGS. 8-12, still another embodiment of the instrument in accordance with the invention is depicted, like reference numerals being applied to like elements. In the embodiment of FIGS. 8-12, housing 12" is provided with a threaded cap 16" to define the hand-held power source 120. Tubular housing 12" is divided in half by a partition 122 extending laterally thereacross. The upper compartment defined by said partition carries the battery 26. Electrical connection to the battery is by means of first contact 124, which projects centrally through and beyond partition 122 for engagement with the positive terminal 30 of battery 26, and a second contact 126, which projects through partition 122 for engagement with a conductive U-shaped member 128. The upper arm of U-shaped member 128 engages spring 40' to provide electrical connection to the negative terminal of battery 26. The lower arm of U-shaped member 128 is formed with a central slot 130 to clear first contact 124.

The compartment defined below partition 122 encloses D.C. motor 24" and a pair of switches 132 and 134. Switch 132 is a reversing switch actuated by a toggle 136 and is in the nature of a double-pole double-throw switch. Switch 134 is an on-off switch operated by pushbutton 138 and is in the nature of a single-pole single-throw switch. The electrical connection is from positive terminal 124 through lead 140 to one contact of switch 132, contact 28' of motor 24' being connected to a corresponding contact of switch 132 through lead 142. The second contact 32' of motor 24" is connected to a third contact of switch 132 by line 144, the corresponding fourth contact of switch 132 being connected to switch 134 by line 146, switch 134 being in turn connected to contact 126 (negative terminal of battery) by line 148. In this manner, pushbutton switch 138 may be actuated to operate the motor, with the direction of rotation of drive shaft 46' being controlled by toggle 136.

Motor 24' and associated circuitry are protected against water leakage through the provision of a resilient gasket 150, through which shaft 46' is journaled. Tubular housing 12" terminates in a truncated conical end wall 18', which in turn terminates in a threaded axially projecting portion 152. A correspondingly threaded fitting 154 supports a first needle 61' and a second needle 70', to which are joined first tube 62' and second tube 74' in a manner equivalent to the arrangement of the embodiment of FIGS. 2-6.

Figure 8:
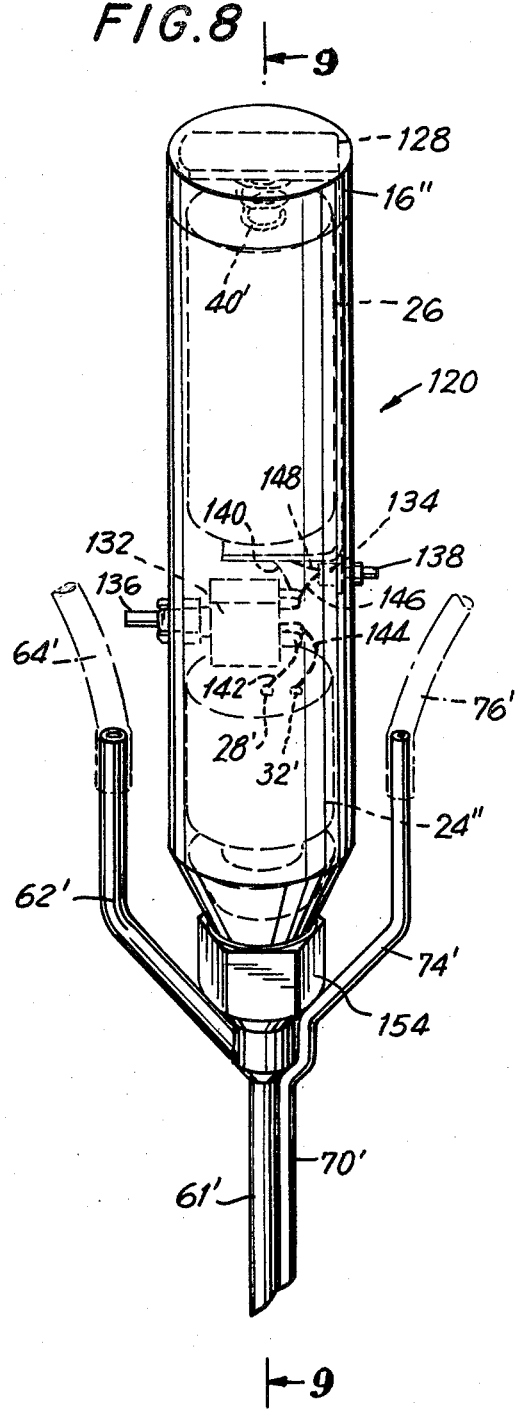
FIG. 8 is a front perspective view of still another alternate embodiment of the device in accordance with the invention.
Figure 9:
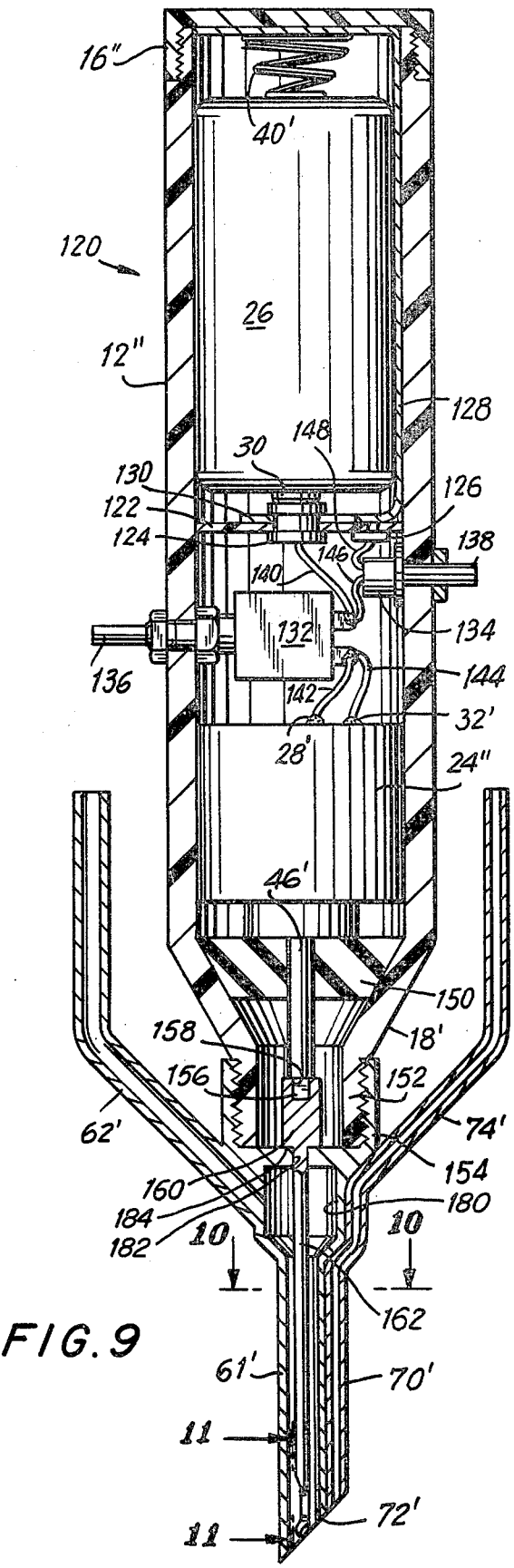
FIG. 9 is a sectional view taken along lines 9—9 of FIG. 8.
Figure 10:
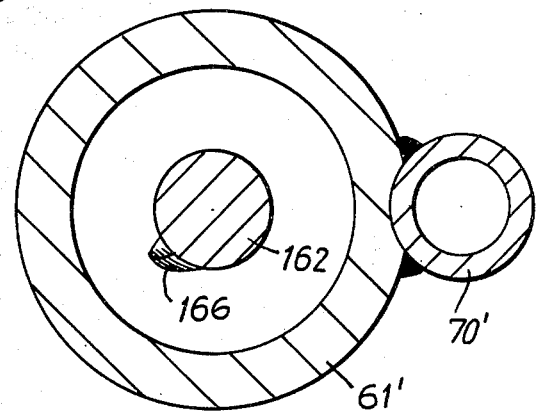
FIG. 10 is an enlarged sectional view taken along lines 10—10 of FIG. 9.
Figure 11:
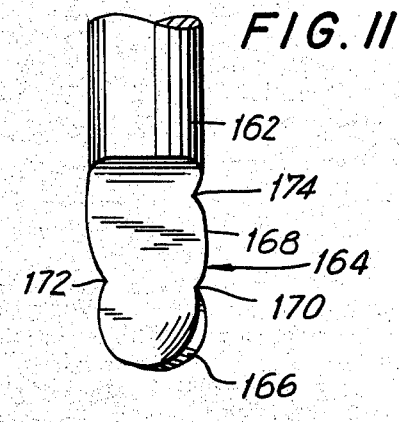
FIG. 11 is a fragmentary sectional view taken along lines 11—11 of FIG. 9 showing the stylus.
Figure 12:
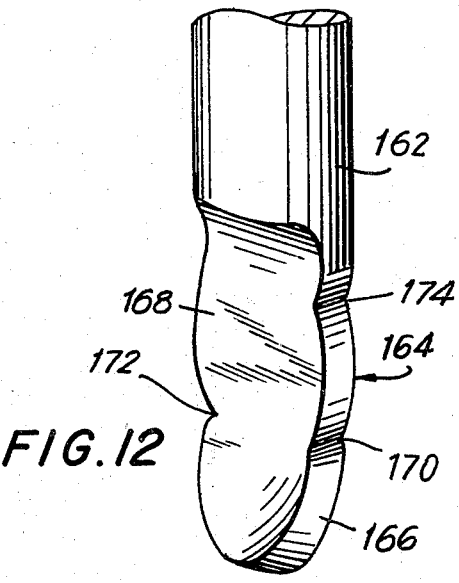
FIG. 12 is an enlarged perspective fragmentary view of the stylus of FIG. 11.

As more particularly shown in FIG. 9, motor drive shaft 46' ends in a stub 156 of non-circular cross-section for receipt in a correspondingly shaped aperture 158 in the base portion 160 of shaft 162. Fitting 154 is formed with an enlarged chamber 180 (FIG. 9) intermediate first tube 62' and first needle 61'. Shaft 162 is journalled through an aperture 182 in end wall 184 defining chamber 180. Shaft 162 differs from shaft 52 of the embodiment of FIGS. 2-6 principally in the configuration of the stylus end thereof. Specifically, as more particularly shown in FIGS. 11 and 12, the stylus 164 of shaft 162 terminates in a "scoop" portion 166 joined to shaft 162 by a substantially flat region 168 and inclined at an angle to the plane defined by the axis of shaft 162 and flat region 168. As is also apparent from a consideration of FIGS. 11 and 12, the scoop portion 166 is also slightly twisted for the purpose of guiding the waste material up through first needle 61'. Notches 170, 172 and 174 are provided staggered on opposed sides along the length of stylus 164, said notches also serving to guide the cut material upwardly. In the embodiment of FIGS. 8-10, the stylus end does not project beyond the beveled ends 72' of needles 61' and 70'.

The embodiment of FIGS. 8-12 is utilized in the same manner as were the embodiments of FIGS. 2-7. As more particularly shown in FIG. 8, first tube 62' is coupled to an exhaust pump through a line 64', shown in phantom, while second tube 74' is joined to a fluid source through line 76', also shown in phantom. Water flow may be controlled by manually bending flexible line 76' or through the provision of an adjustable clamp (not shown) for selectively adjusting the opening in the tube to provide flow between a zero-flow condition and a maximum-flow condition.

It will thus be seen that the objects set forth above, and those made apparent from the preceding description, are efficiently attained, and since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A surgical device for excision of tissue and flushing same away, comprising housing means adapted for support in a hand of a user; motor means mounted in said housing and having a rotatable output shaft projecting through a wall in said housing means; means for powering said motor means in said housing means, said housing means being formed to provide a watertight seal about said motor means shaft extending therethrough; a fitting; releasable coupling means formed in said fitting and in the exterior region of said housing means surrounding said motor shaft extending therethrough for releasably coupling said fitting and said housing means; said fitting being formed with a chamber therein defined, in part, by an end wall formed with an aperture therethrough in registration with said motor means shaft; a first hollow needle mounted on said fitting with its inner end in communication with said chamber and in registration with said aperture and said motor means shaft and its outer end being completely open and free of end wall; a first tube mounted on said fitting and having an inner end communicating with said chamber and an outer end for connection to a vacuum source to decrease the pressure in said chamber and first hollow needle; a rotatable stylus shaft releasably coupled to the end of said motor means shaft projecting outside of said housing means, said stylus shaft being journalled through said end wall aperture and extending through said chamber and first hollow needle, said stylus shaft being shaped to provide a clearance between the side periphery thereof and the inner wall of said first hollow needle for the passage of tissue and fluid therebetween, and being shaped to at least aid in the drawing of tissue from the end thereof to and through a portion of said first needle when said shaft is rotated, the end of said stylus being shaped to cut tissue in contact therewith; a second hollow needle parallel to and secured to said first needle and essentially contiguous therewith; the outer end of said second needle being essentially flush with the outer end of said first needle, the outer ends of said first and second needles being bevelled, the cutting end of said stylus being positioned essentially at the cutaway region defined by the bevel in the end of said first needle; a second tube mounted on said fitting for support thereby and having an inner end coupled to the inner end of said second hollow needle and its outer end adapted for connection to a source of washing fluid; whereby the combination of introduction of washing fluid into the vicinity of the cutting end of said stylus shaft when rotating, a drop of pressure in said first hollow needle and the operation of said stylus shaft results in the flushing away through said first hollow needle, said fitting chamber and out said first tube of tissue excised by said rotating stylus shaft and fluid associated therewith, and whereby said fitting, first and second tubes and first and second hollow needles may be removed from said housing as a unit.

2. The surgical device as claimed in claim 1, wherein said source of washing fluid is a reservoir positioned above said second tube so that flow of washing fluid is the result of gravity.

3. The surgical device as claimed in claim 1, wherein said outer ends of said first and second needles and any coupling material therebetween are beveled in the same plane.

4. The surgical device as claimed in claim 1, wherein said means for powering said motor means comprises battery means mounted within said housing means.

5. The surgical device as claimed in claim 4, and including manually operable switch means mounted on the exterior of said housing means and electrically connected through said housing means to said motor means and battery means.

6. The surgical device as claimed in claim 5, including reversal switch means carried on said housing means for permitting selective reversal of the direction of rotation of said motor means, and therefore said stylus shaft.

7. The surgical device as claimed in claim 4, and including means for controlling the flow of washing fluid through said second tube.

8. The surgical device as claimed in claim 1, wherein said means powering said motor means comprises electrical power cord means extending through the wall of said housing means.

9. A device as claimed in claim 1, wherein said first tube is formed with an aperture in the wall thereof at a location proximate to a finger of the hand of a user holding said housing means for the selective closing of said aperture, whereby the pressure within said chamber and first hollow needle is selectively controlled by the selective opening and closing of said aperture in said first tube.

10. The surgical device as claimed in claim 1, wherein said first hollow needle is a number 16 needle having an outer diameter of about 0.070 inches and an inner diameter of about 0.052 inches, said stylus shaft having a diameter of about 0.38 inches, and said cutting end of said stylus shaft being the flattened end of said shaft, said flattened end having a width of about 0.047 inches.

11. The surgical device as claimed in claim 1, wherein said stylus shaft is formed from a cylindrical rod, the cutting end of said stylus shaft being the flattened and twisted end of said rod.

* * * * *